US011887730B2

(12) United States Patent
Ghose et al.

(10) Patent No.: US 11,887,730 B2
(45) Date of Patent: Jan. 30, 2024

(54) SYSTEMS AND METHODS FOR UNOBTRUSIVE DIGITAL HEALTH ASSESSMENT

(71) Applicant: Tata Consultancy Services Limited, Mumbai (IN)

(72) Inventors: Avik Ghose, Kolkata (IN); Arpan Pal, Kolkata (IN); Sundeep Khandelwal, Noida (IN); Rohan Banerjee, Kolkata (IN); Sakyajit Bhattacharya, Kolkata (IN); Soma Bandyopadhyay, Kolkata (IN); Arijit Ukil, Kolkata (IN); Dhaval Satish Jani, Rockville, MD (US)

(73) Assignee: Tata Consultancy Services Limited, Mumbai (IN)

( * ) Notice: Subject to any disclaimer, the term of this patent is extended or adjusted under 35 U.S.C. 154(b) by 1026 days.

(21) Appl. No.: 16/526,340

(22) Filed: Jul. 30, 2019

(65) Prior Publication Data
US 2020/0034690 A1 Jan. 30, 2020

(30) Foreign Application Priority Data
Jul. 30, 2018 (IN) .............................. 201821028541

(51) Int. Cl.
*G16H 50/20* (2018.01)
*G16H 50/70* (2018.01)
(Continued)

(52) U.S. Cl.
CPC ............. *G16H 50/20* (2018.01); *G06N 3/043* (2023.01); *G16H 50/70* (2018.01); *G06N 20/00* (2019.01)

(58) Field of Classification Search
CPC ............................... G16H 50/20; G06N 20/00
(Continued)

(56) References Cited

U.S. PATENT DOCUMENTS 9,554,738 B1 * 1/2017 Gulati .................. A61B 5/0075
2009/0054737 A1 2/2009 Magar et al.
(Continued)

FOREIGN PATENT DOCUMENTS

WO WO-2018129481 A2 * 7/2018 ............... G06N 5/04

OTHER PUBLICATIONS

Tom Fawcett, "Learning from Imbalanced Classes," Silicon Valley Data Science, Aug. 25, 2016 available at https://www.svds.com/learning-imbalanced-classes/ (Year: 2016).*
(Continued)

*Primary Examiner* — Hiep V Nguyen
(74) *Attorney, Agent, or Firm* — Finnegan, Henderson, Farabow, Garrett & Dunner, LLP

(57) ABSTRACT

This disclosure relates generally to methods and systems for unobtrusive digital health assessment of high risk subjects, wherein bio-markers pertaining to a disease are identified automatically using physical activity and physiology monitoring on a continuous basis. Identification of bio-markers in the medical domain is conventionally dependent on insights derived from medical tests which are obtrusive in nature. Systems and methods of the present disclosure integrate physical characteristics, lifestyle habits and prevailing medical conditions with monitored physical activities and physiological measurements to assess health of high risk subjects. Systems and methods of the present disclosure also enable automatic generation of control class and treatment class that may be effectively used for health assessment.

9 Claims, 16 Drawing Sheets

(51) Int. Cl.
*G06N 3/043* (2023.01)
*G06N 20/00* (2019.01)

(58) Field of Classification Search
USPC .............................................. 705/2
See application file for complete search history.

(56) References Cited

U.S. PATENT DOCUMENTS

2012/0259651 A1  10/2012  Mallon et al.
2014/0046683 A1*  2/2014  Michelson ............. G16B 40/00
                                                    705/2
2016/0252484 A1*  9/2016  Rubinstein ......... G01N 30/8693
                                                    702/19

OTHER PUBLICATIONS

Malec, Carol Anne; The effect of a healthy lifestyle intervention on quality of life in the chronically ill: A Randomized Control Trial; University of Calgary (Canada). ProQuest Dissertations Publishing, 2002. NQ77029. (Year: 2002).*

Zheng, Y. et al. (Mar. 2014). "Unobtrusive Sensing and Wearable Devices for Health Informatics," *IEEE Transactions on Biomedical Engineering*, vol. 61, No. 5; pp. 1538-1554.

* cited by examiner

SYSTEMS AND METHODS FOR UNOBTRUSIVE DIGITAL HEALTH ASSESSMENT

PRIORITY CLAIM

This U.S. patent application claims priority under 35 U.S.C. § 119 to: Indian Patent Application No. 201821028541, filed on 30 Jul. 2018. The entire contents of the aforementioned application are incorporated herein by reference.

TECHNICAL FIELD

The disclosure herein generally relates to health assessment, and, more particularly, to a platform that facilitates screening of high risk subjects by monitoring their daily lives in an unobtrusive manner.

BACKGROUND

Existing healthcare systems are mostly based on reactive medicine whereby person goes to a medical practitioner only when she is symptomatic. Another approach relies on periodic health checkups in an attempt to discover medical conditions at an early stage. Both the approaches have some issues. The first approach suffers from the fact that by the time some diseases become symptomatic, considerable damage may have already been done. An issue with the second approach is that since patient is asymptotic, the checkups may result in no diagnosis at all; the fallout rate is also high owing to people's busy schedules.

SUMMARY

Embodiments of the present disclosure present technological improvements as solutions to one or more of the above-mentioned technical problems recognized by the inventors in conventional systems.

In an aspect, there is provided a processor implemented method comprising: obtaining values associated with a plurality of metadata features, wherein the plurality of metadata features constitute domain knowledge of high risk subjects under consideration and comprise one or more of physical characteristics, lifestyle habits and prevailing medical conditions; generating groups of the high risk subjects under consideration based on a plurality of combinations of the obtained plurality of metadata features; and iteratively obtaining a skewed normal distribution of the high risk subjects to generate a treatment class and a control class for each of the generated groups, the step of obtaining a skewed normal distribution comprising: generating a fuzzy membership function based on a neural network and deriving two feature classes for each of the obtained metadata features; deriving a plurality of normalized values between 0 and 1 for each of the high risk subjects in the two derived feature classes, wherein a normalized value in the plurality of normalized values corresponds to a metadata feature; obtaining a Manhattan distance between every pair of subjects amongst the high risk subjects using the plurality of normalized values; generating two clusters of the high risk subjects based on the obtained Manhattan distance and using a fuzzy C-means clustering method such that each of the two clusters have equivalent normalized values; randomly sampling the two clusters to create the control class and the treatment class such that the control class and the treatment class comprises an equivalent number of high risk subjects from each of the two clusters; and reconstructing the plurality of normalized values associated with each of the high risk subjects to obtain actual values corresponding to the associated metadata features for each of the high risk subjects in the control class and the treatment class.

In another aspect, there is provided a system comprising: one or more data storage devices operatively coupled to the one or more processors and configured to store instructions configured for execution by the one or more processors to: obtain values associated with a plurality of metadata features, wherein the plurality of metadata features constitute domain knowledge of high risk subjects under consideration and comprise one or more of physical characteristics, lifestyle habits and prevailing medical conditions; generate groups of the high risk subjects under consideration based on a plurality of combinations of the obtained plurality of metadata features; and iteratively obtain a skewed normal distribution of the high risk subjects to generate a treatment class and a control class for each of the generated groups, wherein the skewed normal distribution is obtained by: generating a fuzzy membership function based on a neural network and deriving two feature classes for each of the obtained metadata features; deriving a plurality of normalized values between 0 and 1 for each of the high risk subjects in the two derived feature classes, wherein a normalized value in the plurality of normalized values corresponds to a metadata feature; obtaining a Manhattan distance between every pair of subjects amongst the high risk subjects using the plurality of normalized values; generating two clusters of the high risk subjects based on the obtained Manhattan distance and using a fuzzy C-means clustering method such that each of the two clusters have equivalent normalized values; randomly sampling the two clusters to create the control class and the treatment class such that the control class and the treatment class comprises an equivalent number of high risk subjects from each of the two clusters; and reconstructing the plurality of normalized values associated with each of the high risk subjects to obtain actual values corresponding to the associated metadata features for each of the high risk subjects in the control class and the treatment class.

In yet another aspect, there is provided a computer program product comprising a non-transitory computer readable medium having a computer readable program embodied therein, wherein the computer readable program, when executed on a computing device, causes the computing device to: obtain values associated with a plurality of metadata features, wherein the plurality of metadata features constitute domain knowledge of high risk subjects under consideration and comprise one or more of physical characteristics, lifestyle habits and prevailing medical conditions; generate groups of the high risk subjects under consideration based on a plurality of combinations of the obtained plurality of metadata features; and iteratively obtain a skewed normal distribution of the high risk subjects to generate a treatment class and a control class for each of the generated groups, wherein the skewed normal distribution is obtained by: generating a fuzzy membership function based on a neural network and deriving two feature classes for each of the obtained metadata features; deriving a plurality of normalized values between 0 and 1 for each of the high risk subjects in the two derived feature classes, wherein a normalized value in the plurality of normalized values corresponds to a metadata feature; obtaining a Manhattan distance between every pair of subjects amongst the high risk subjects using the plurality of normalized values; generating two clusters of the high risk subjects based on the obtained Manhattan distance and using a fuzzy C-means clustering method such that each of the two clusters have equivalent normalized values; randomly sampling the two clusters to create the control class and the treatment class such that the control class and the treatment class comprises an equivalent number of high risk subjects from each of the two clusters; and reconstructing the plurality of normalized values associated with each of the high risk subjects to obtain actual values corresponding to the associated metadata features for each of the high risk subjects in the control class and the treatment class.

In an embodiment of the present disclosure, the one or more hardware processors are further configured to obtain values associated with a plurality of metadata features by (i) directly deriving the values using corresponding measurement devices or (ii) estimating the values based on the domain knowledge of the high risk subjects under consideration.

In an embodiment of the present disclosure, the one or more hardware processors are further configured to randomly sample the two clusters based on a mean and a standard deviation associated with the obtained skewed normal distribution of the high risk subjects.

In an embodiment of the present disclosure, the neural network uses a multi-layer perceptron with at least two hidden layers and a fully connected input and output layer.

In an embodiment of the present disclosure, the one or more hardware processors are further configured to identify a level of deterioration of health of each of the high risk subjects in the treatment class by: monitoring physical activity levels and physiological measurements of the high risk subjects from the treatment class; classifying each of the high risk subjects into one of a plurality of pre-determined classes illustrative of health assessment thereof using a computational model and a correlation between the monitored physical activity levels and the physiological measurements; predicting a normalized value for each of the physiological measurements of interest using a Hidden Markov Model (HMM); and computing a measure of deviation from the predicted normalized value using an actual normalized value obtained from the monitoring physiological measurements to assess deviation from a healthy condition for each of the high risk subjects and identifying an associated metadata feature as a bio-marker for further assessment of a corresponding high risk subject.

In an embodiment of the present disclosure, the one or more hardware processors are further configured to eliminate local outliers in the physiological measurements using a Local Outlier Filter (LOF) algorithm to obtain filtered physiological measurements; perform a trend analyses, of the monitored physical activity levels and the filtered physiological measurements, using AutoRegressive Integrated Moving Average (ARIMA); and trigger an alarm when a trend is negative with a slope greater than a pre-defined threshold.

In an embodiment of the present disclosure, the one or more hardware processors are further configured to compute a measure of deviation from the predicted value by analyzing feedback pertaining to intensity associated with the monitored physical activity levels from the high risk subjects.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
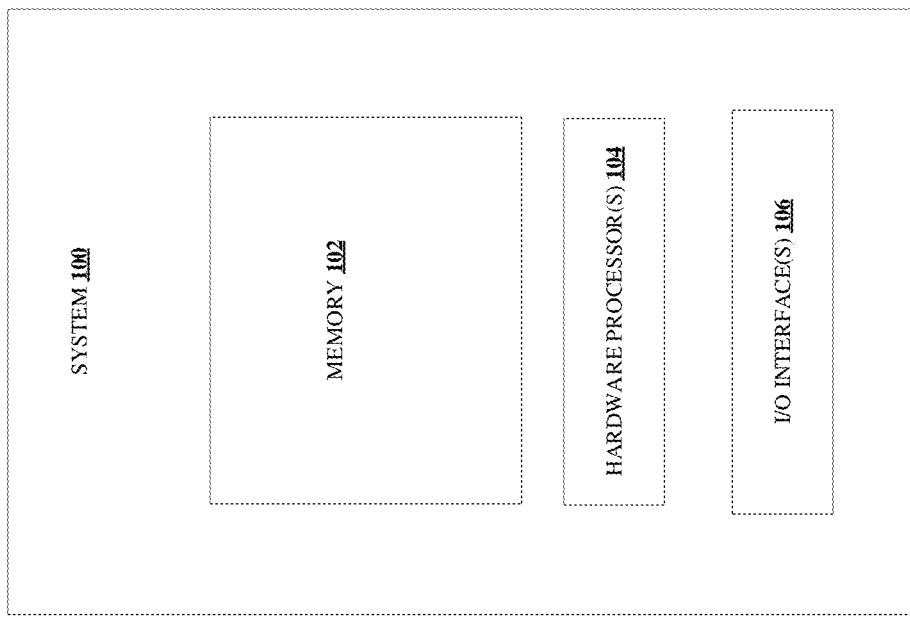
FIG. 1 illustrates an exemplary block diagram of a system for unobtrusive digital health assessment, in accordance with an embodiment of the present disclosure.
Figure 2A:
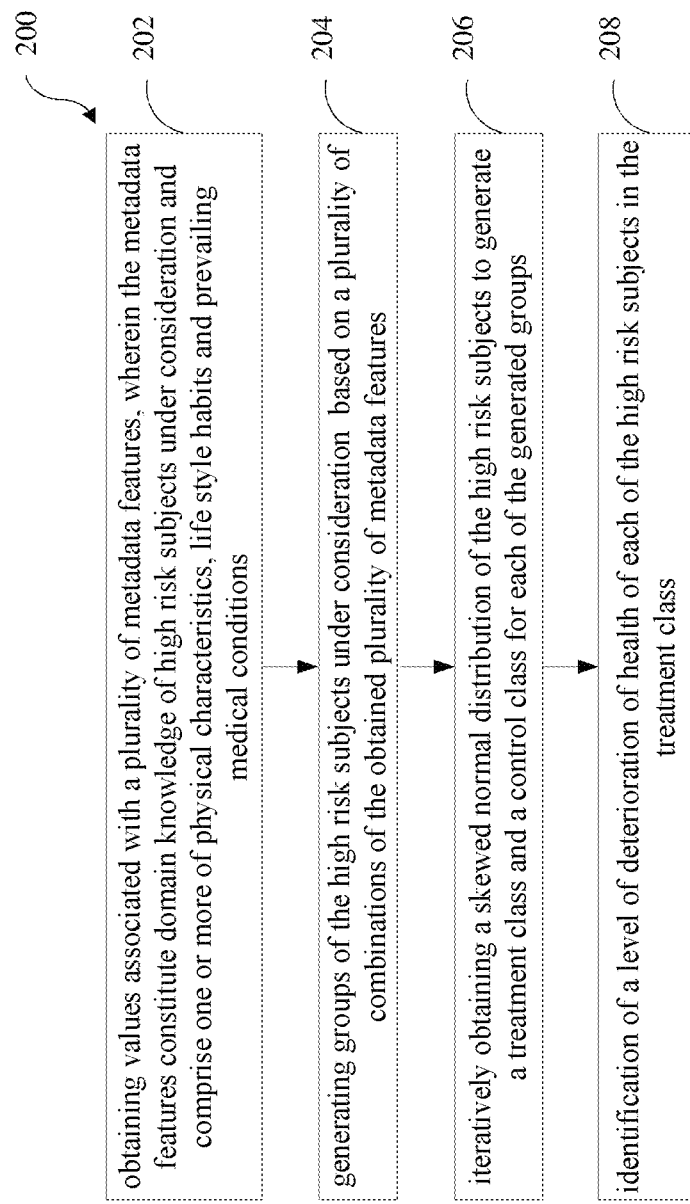
FIG. 2A through FIG. 2D illustrate exemplary flow charts for a computer implemented method for unobtrusive digital health assessment, in accordance with an embodiment of the present disclosure.
Figure 2B:
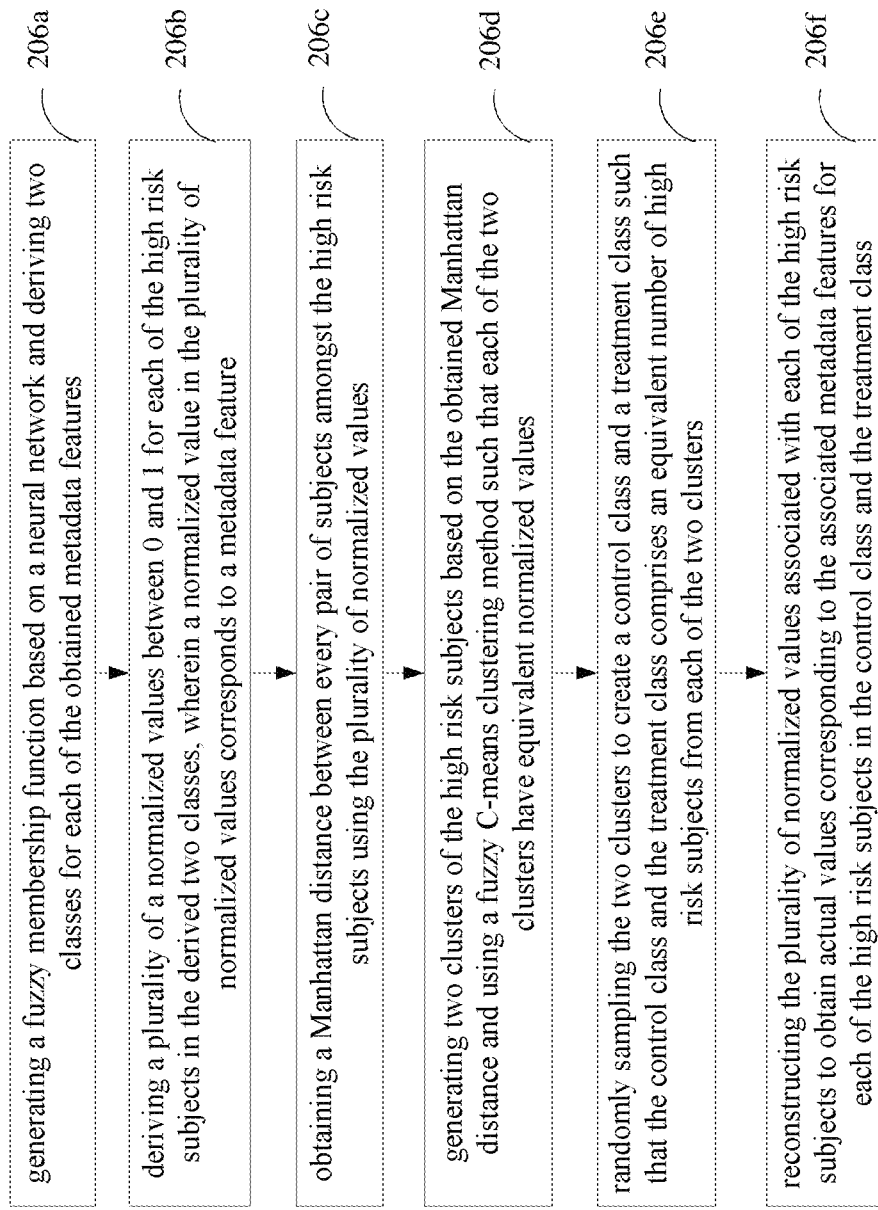
Figure 2C:
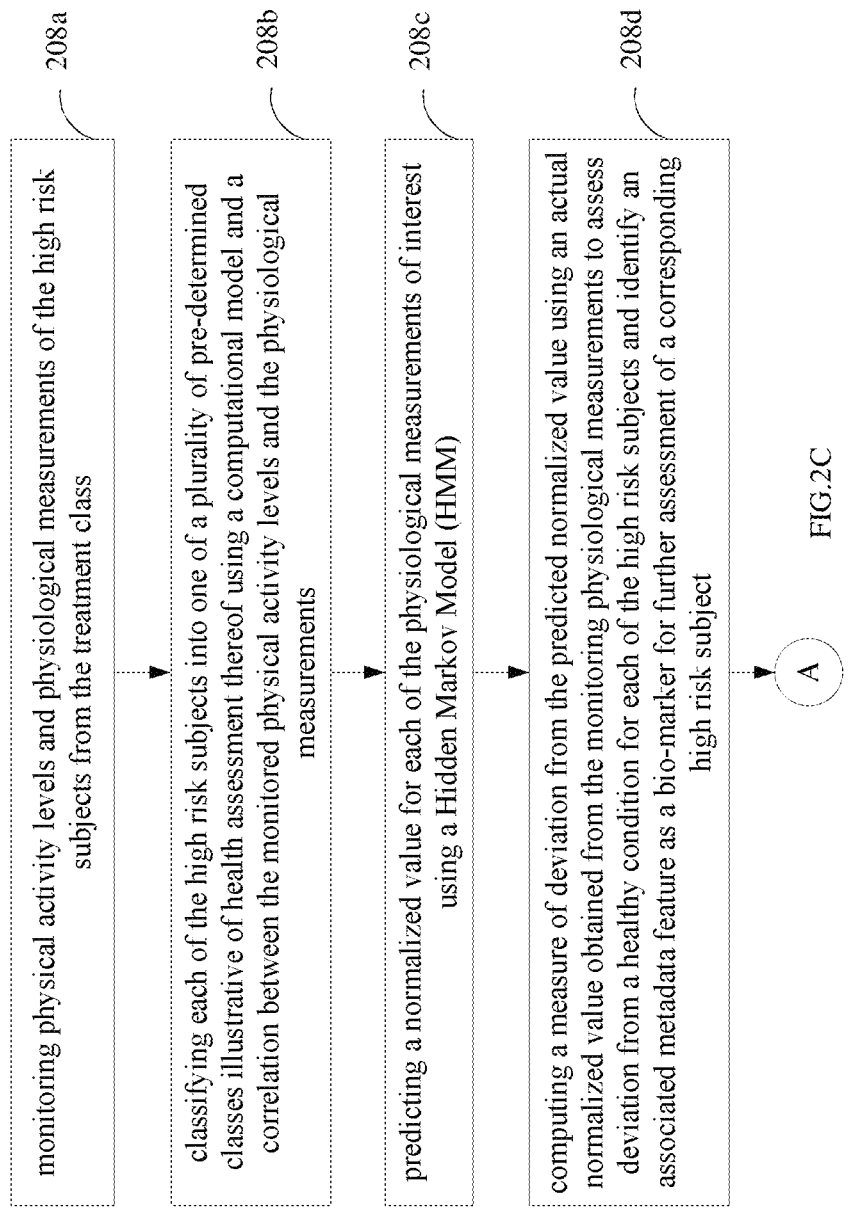
Figure 2D:
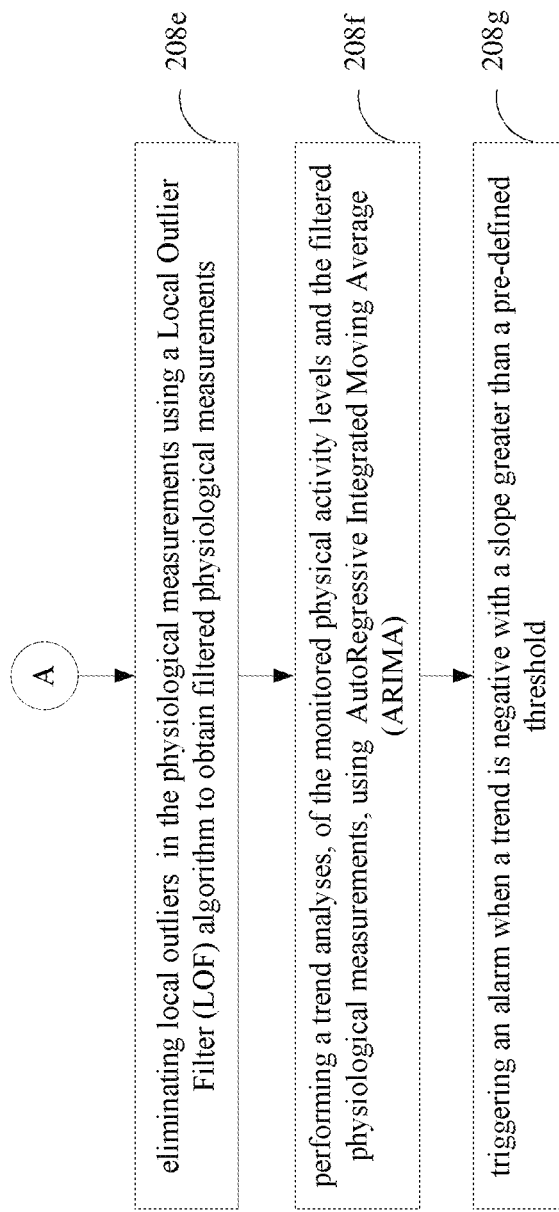

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Systems and methods of the present disclosure enable screening of diseases in high risk subjects by monitoring their daily life. In the context of the present disclosure, the expression 'high risk subjects' are subjects with predisposing systemic conditions including neuropathy, peripheral arterial disease, diabetes mellitus, proneness to infection, autoimmune disease and immunocompromised rendering them more likely than others to get a particular disease. The present disclosure enables a platform that integrates physical characteristics, lifestyle habits and prevailing medical conditions with monitored physical activities and physiological measurements to assess health of high risk subjects. In the context of the present disclosure, the physical characteristics may include height, weight, gender, ethnicity, age and the like. Likewise, lifestyle habits may include smoking, drinking, exercising regularly, over-eating, and the like. Further, in the context of the present disclosure, prevailing medical conditions may include diabetes, hypertension, cardiac illness, anemia, and the like.

Referring now to the drawings, and more particularly to FIGS. 1 through 9B, where similar reference characters denote corresponding features consistently throughout the figures, there are shown preferred embodiments and these embodiments are described in the context of the following exemplary system and method.

FIG. 1 illustrates an exemplary block diagram of a system 100 for for unobtrusive digital health assessment in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

FIG. 2 is an exemplary flow diagram illustrating a computer implemented method for unobtrusive digital health assessment, in accordance with an embodiment of the present disclosure. In an embodiment, the system 100 includes one or more data storage devices or memory 102 operatively coupled to the one or more processors 104 and is configured to store instructions configured for execution of steps of the method 200 by the one or more processors 104. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Accordingly, in an embodiment of the present disclosure, the one or more processors 104 are configured to obtain, at step 202, values associated with a plurality of metadata features, wherein the plurality of metadata features constitute domain knowledge of high risk subjects under consideration and comprise one or more of physical characteristics, lifestyle habits and prevailing medical conditions. The step of obtaining values may comprise directly deriving the values using corresponding measurement devices. Alternatively, the values may be estimated based on the domain knowledge of the high risk subjects under consideration.

In an embodiment of the present disclosure, the one or more processors 104 are configured to generate, at step 204, groups of the high risk subjects under consideration based on a plurality of combinations of the obtained plurality of metadata features. For instance, there may be a group of age 40+ high risk subjects, a group of age 40+ high risk subjects with weight 80+kg, a group of age 40+ high risk subjects with height more than 6 feet, a group of age 40+ high risk subjects with weigh 80+kg and having cardiac issues, and the like.

Figures 3A, 3B:
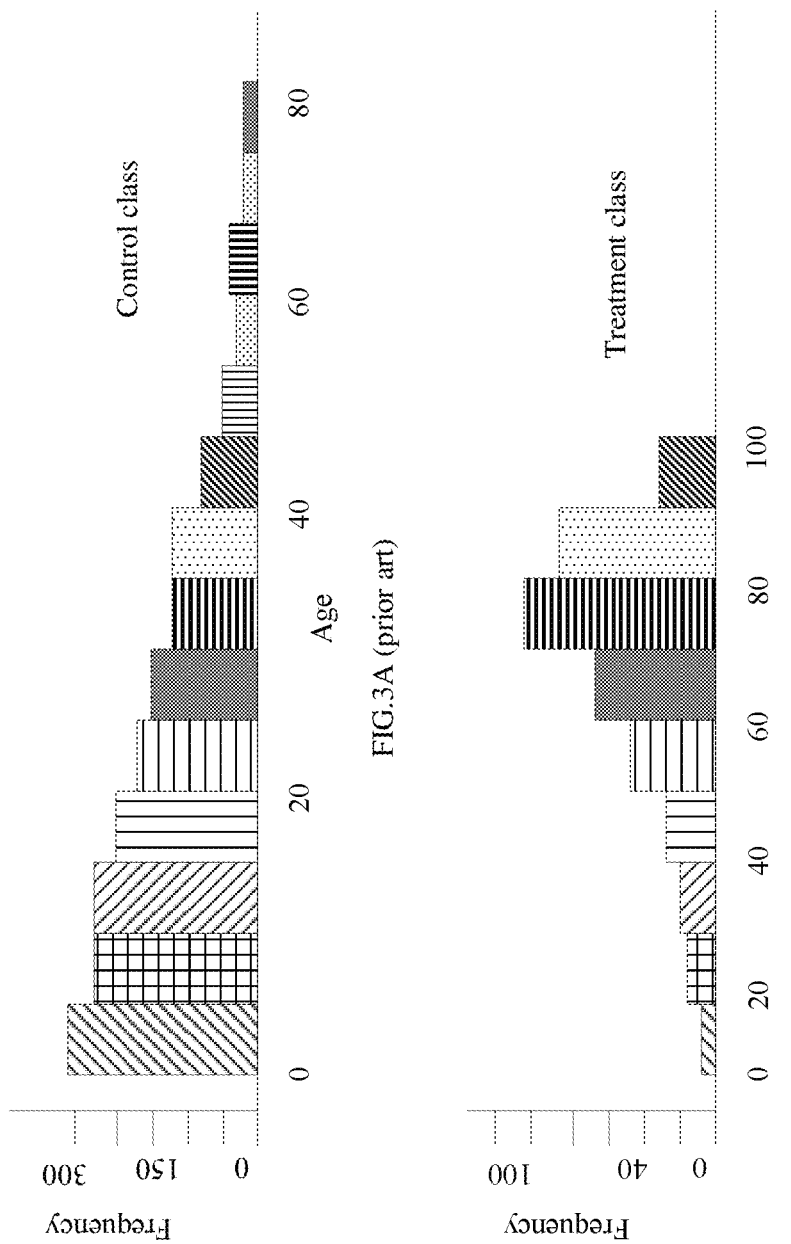
FIG. 3A and FIG. 3B illustrate an exemplary control class and an exemplary treatment class respectively of high risk subjects obtained in the art.

Say, there is a dataset of subjects, some of which have a certain disease and some who do not have the disease. Let these two classes be denoted as 1 and 0, respectively. Metadata features of the high risk subjects in both classes may be obtained. For instance, say age information is obtained. Given the disease population (class 1), it is critical to decide whether the control class (class 0) is close to the treatment class, or far, based on the distribution of the metadata features. This involves generating a control class so that the correlation coefficient between the distributions of the metadata features of both classes is close to 1. FIG. 3A and FIG. 3B illustrate an exemplary control class and an exemplary treatment class respectively of high risk subjects obtained in the art, wherein age information as a metadata feature was simulated for heart disease patients from different countries. Originally, the treatment and control classes were of the size 480 and 1528 and the distributions are as illustrated in FIG. 3A and FIG. 3B respectively. It may be noted that the control class distribution resembles a decaying power law relation whereas the treatment class is the opposite giving an impression that age may be a driving factor for the disease. Grouping of subjects automatically based on metadata features is challenging because unsupervised grouping is performed using clustering techniques and metadata features are often categorical or subjective.

In accordance with the present disclosure, various embodiments of the system 100 and method 200 explained hereinafter facilitate automatic generation of a treatment class and a control class which can ultimately result in identifying bio-markers for further assessment of the high risk subjects. Accordingly, in an embodiment, the one or more processors 104 are configured to iteratively obtain, at step 206, a skewed normal distribution of the high risk subjects to generate the treatment class and the control class for each of the groups generated at step 204. The step 206 addresses the issue seen in FIG. 3A and FIG. 3B explained herein above. Histogram information of binned data of both classes pertaining to the distribution of the metadata features may be used. The control class may be generated such that a ratio of the bins in its histogram is close to the ratio of bins in the treatment population histogram. It may be mathematically shown that for large treatment and control classes (size<=50), the correlation between the classes is close to 1.

Figure 4A:
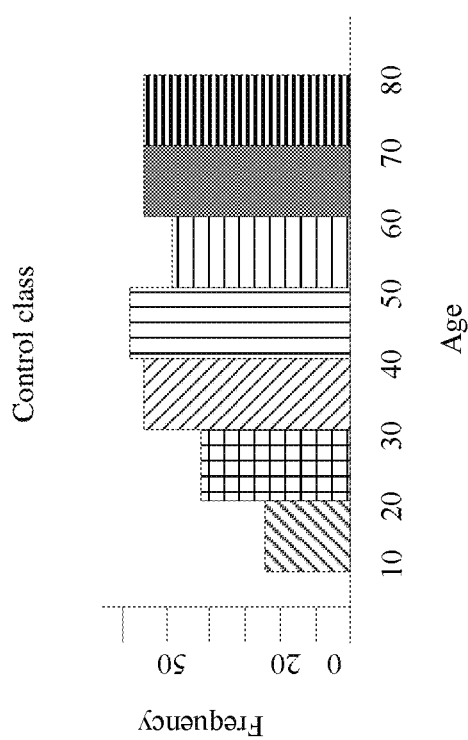
FIG. 4A and FIG. 4B illustrate a skewed normal distribution of the high risk subjects in a control class and a treatment class respectively of high risk subjects obtained in accordance with an embodiment of the present disclosure.
Figure 4B:
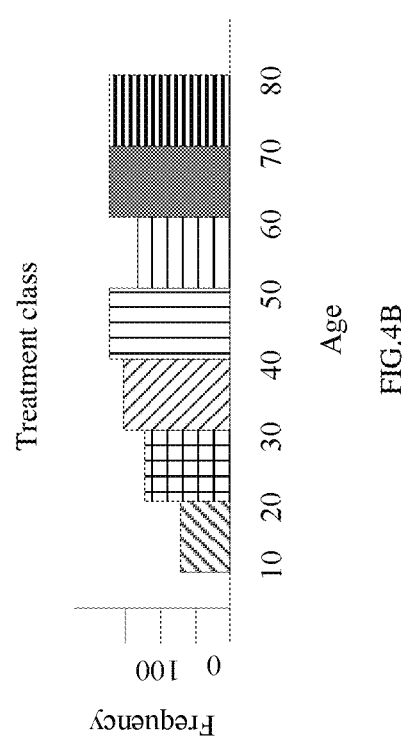

Particularly, as part of step 206, in an embodiment, firstly a fuzzy membership function based on a neural network is generated at step 206a and two feature classes are derived for each of the obtained metadata features. For instance, the classes may be young/old for age as a metadata feature, the classes may be tall/short for height as a metadata feature, and the like. In an embodiment, the neural network uses a multi-layer perceptron with at least two hidden layers and a fully connected input and output layer. At step 206b, a plurality of normalized values between 0 and 1 are derived for each of the high risk subjects in the two derived feature classes, wherein a normalized value in the plurality of normalized values corresponds to a metadata feature. For instance, hypothetically speaking, if thin is 0 and fat is 1 for body type as a metadata feature and say if old is 0 and young is 1, a high risk subject who is thin and old may have normalized values like 0.2 thin, 0.8 old. At step 206c, a Manhattan distance between every pair of subjects amongst the high risk subjects is obtained using the plurality of normalized values derived at step 206b. Two clusters of the high risk subjects are then generated at step 206d based on the obtained Manhattan distance and using a fuzzy C-means clustering method such that each of the two clusters have equivalent normalized values. The fuzzy C-means clustering ensures inter-cluster distance is high whereas intra-cluster distance is low. The two clusters generated at step 206d are then randomly sampled at step 206e to create the control class and the treatment class such that both the classes comprise an equivalent number of high risk subjects from each of the two clusters. FIG. 4A and FIG. 4B illustrate a skewed normal distribution of the high risk subjects in a control class and a treatment class respectively of high risk subjects obtained in accordance with an embodiment of the present disclosure. In an embodiment, the random sampling is based on a mean and a standard deviation associated with the obtained skewed normal distribution of the high risk subjects. Once the treatment and control classes are created, the plurality of normalized values associated with each of the high risk subjects are reconstructed at step 206f to obtain actual values corresponding to the associated metadata features for each of the high risk subjects in the control class and the treatment class. In an embodiment, the reconstruction may involve correlating an identifier of a subject with a meta-dictionary.

If the normal for a particular subject is personalized and if an attempt is made to derive abnormal with respect to the normal, it may be noted that outliers and abnormal readings due to temporary health problems may be captured. This anomaly may be averted by taking a longer measurement and running a Local Outlier Filter (LOF) algorithm over a time series. However, quantifying deviation to gauge a level of deterioration of health is a challenge. In accordance with an embodiment of the present disclosure, the method 200 further comprises a step 208, wherein the one or more processors 104 are configured to identify the level of deterioration of health of each of the high risk subjects in the treatment class. Towards this, firstly physical activity levels and physiological measurements of the high risk subjects from the treatment class maybe monitored at step 208a. For instance, how long and what distance has the high risk subject walked today may be measured. Such monitoring may be performed using wearable devices and allied mobile or stationary gateways.

In accordance with an embodiment of the present disclosure, each of the high risk subjects may then be classified at step 208b into one of a plurality of pre-determined classes illustrative of health assessment of the high risk subject. This classification may be performed using a computational model and a correlation between the monitored physical activity levels and the physiological measurements. In an embodiment, the computation model may be based on New York Heart Association (NYHA) guidelines wherein 4 classes are identified to depict stages of heart failure. As per NYHA guidelines, Class I is mapped to a condition that ordinary physical activity does not cause undue fatigue, palpitations, dyspnea and/or angina; Class II is mapped to a condition that ordinary physical activity does cause undue fatigue, palpitations, dyspnea and/or angina; Class III is mapped to a condition that less than ordinary physical activity causes undue fatigue, palpitations, dyspnea and/or angina; and Class IV is mapped to a condition that fatigue, palpitations, dyspnea and/or angina occurs at rest. In an embodiment, a metadata feature fatigue may be modelled in the form of I=f (MET, W, T, LPA, G, A, N), wherein I represents intensity as a function of intensity associated with the monitored physical activity levels (MET), W represents body weight of the high risk subject under consideration, T represents Spell's duration, LPA represents level of physical activity in daily life of the high risk subject under consideration, G represents gender of the high risk subject under consideration, A represents age spectrum and N represents a normalization constant.

In accordance with an embodiment of the present disclosure, at step 208c, a normalized value for each of the physiological measurements is predicted using a Hidden Markov Model (HMM). In an embodiment, the prediction using HMM may be performed using stage wise prediction, the parameters being MET, breathing power change, heart rate change, breathing rate change and time taken to return to a Basal heart rate (normal heart rate at rest for the high risk subject under consideration). Accordingly, Class II may be identified if a high risk subject gets tired after say 6 minutes (to be normalized) of walking.

In accordance with an embodiment, at step 208d, a measure of deviation from the predicted normalized value using an actual normalized value obtained from the monitoring physiological measurements is computed. In an embodiment, the deviation may be computed as a mean deviation wherein lower quadrant values may be considered and upper quadrant values are only be considered if no lower quadrant values are available. The measure of deviation may then be used to assess deviation from a healthy condition for each of the high risk subjects and to identify an associated metadata feature as a bio-marker for further assessment of a corresponding high risk subject. For instance, in Class II ordinary physical activity does cause undue fatigue, palpitations, dyspnea and/or angina. If the subject does get tired after an ordinary physical activity like say after 2 minutes of walking, the high risk subject may be classified into Class II. Optionally, a feedback may be requested, from the high risk subject pertaining to MET may be analyzed and whether he does feel tired after 2 minutes of walking as measured. Also, a metadata feature associated with the tiredness may be identified as a bio-marker for further assessment of a corresponding high risk subject.

In an embodiment, local outliers may be eliminated, at step 208e, in the physiological measurements using a Local Outlier Filter (LOF) algorithm to obtain filtered physiological measurements. A trend analyses may be performed, at step 208f, of the monitored physical activity levels and the filtered physiological measurements using AutoRegressive Integrated Moving Average (ARIMA). For instance, some days the high risk subject may have a headache leading to spikes in the trend analyses which clearly need to be ignored. Each of the high risk subjects may have different energy levels at different times of the day or may have seasonal variations leading to a trend. Over time, a subject may get more tired and such long term trend may be identified using ARIMA. At step 208g, an alarm may be triggered when the trend is negative with a slope greater than a pre-defined threshold.

Figure 5:
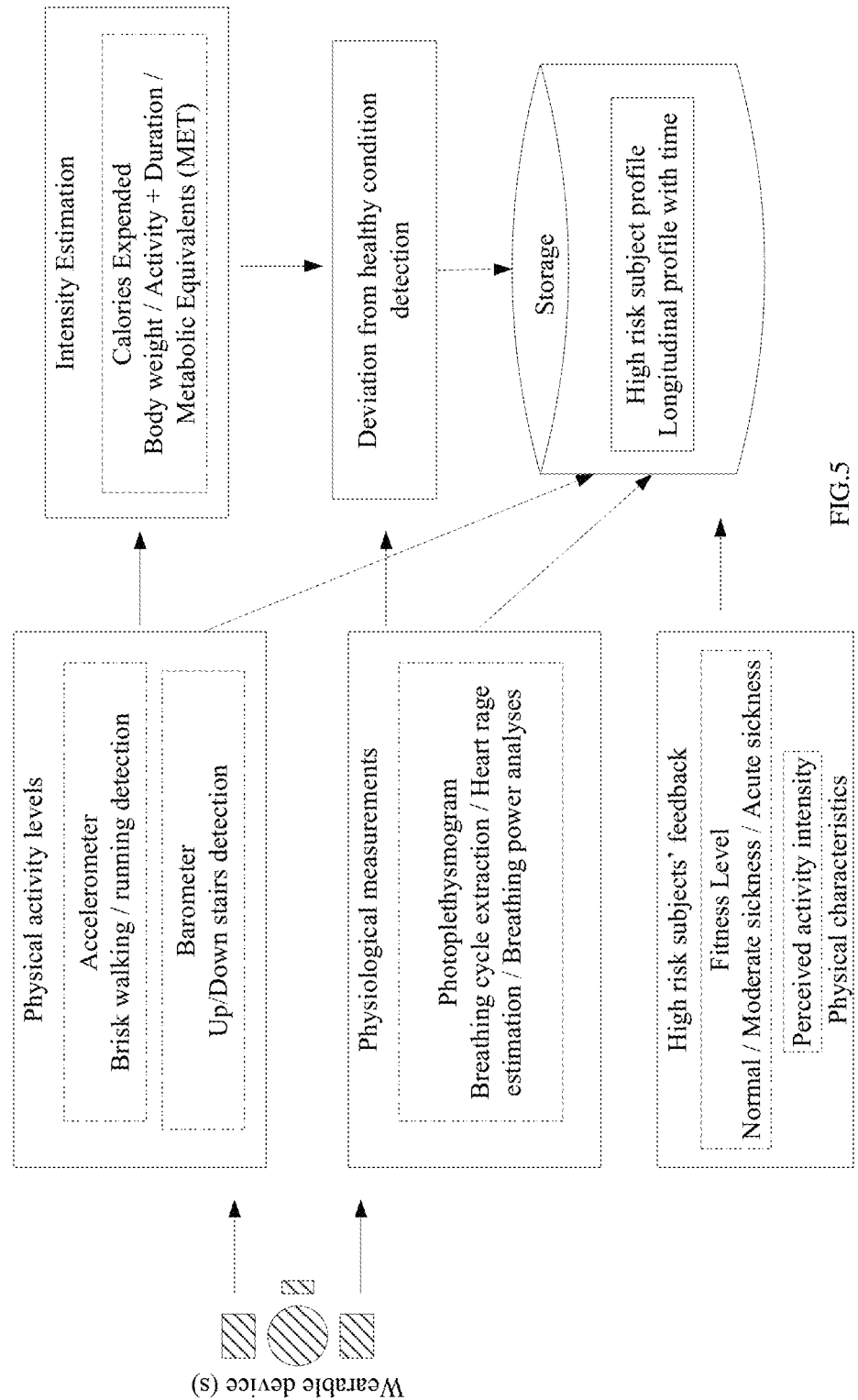
FIG. 5 illustrates a schematic representation of a high level implementation of the method illustrated in FIG. 2A through FIG. 2D for unobtrusive digital health assessment in accordance with an embodiment of the present disclosure.

Thus, in accordance with the present disclosure, systems and methods of the present disclosure may find application in both pre-op and post-op scenarios. FIG. 5 illustrates a schematic representation of a high level implementation of the method illustrated in FIG. 2A through FIG. 2D for unobtrusive digital health assessment in accordance with an embodiment of the present disclosure. In an embodiment, physiological parameters when monitored before and after an activity for a particular MET may be used to assess the levels of cardiopulmonary fatigue in a high risk subject under consideration who otherwise appears asymptomatic. The fatigue levels of the high risk subject under consideration may then be normalized considering other high risk subjects in the same group as explained above. If the normalized level of fatigue is higher than a major percentage of population in the group, the high risk subject may be marked for further assessment based on fatigue level being identified as a bio-marker. Such marked high risk subjects may be monitored longitudinally over time to check if the fatigue levels are trending negatively to trigger a timely alarm. If the fatigue levels are not trending negatively, the pre-op monitoring may continue assessing the health of the high risk subject in an unobtrusive manner as explained. Conventionally, identifying a bio-marker may involve insights derived through obtrusive medical tests and correlating such insights with activities of daily living (ADL) is a challenge. Post-op care of a high risk subject is more vital and risk prone. Accordingly, the systems and methods of the present disclosure may comprise accurate monitoring of movement patterns using devices such as Kinect and the physiological parameters may also be checked using sophisticated medical devices (for instance, measuring of blood oxygen saturation levels SpO2). In an embodiment, a persuasion engine (not shown) may be comprised in the system 100 to involve a care taker for the high risk subject under consideration for ensuring post-op care and requirements are adhered without fail.

Figure 6A:
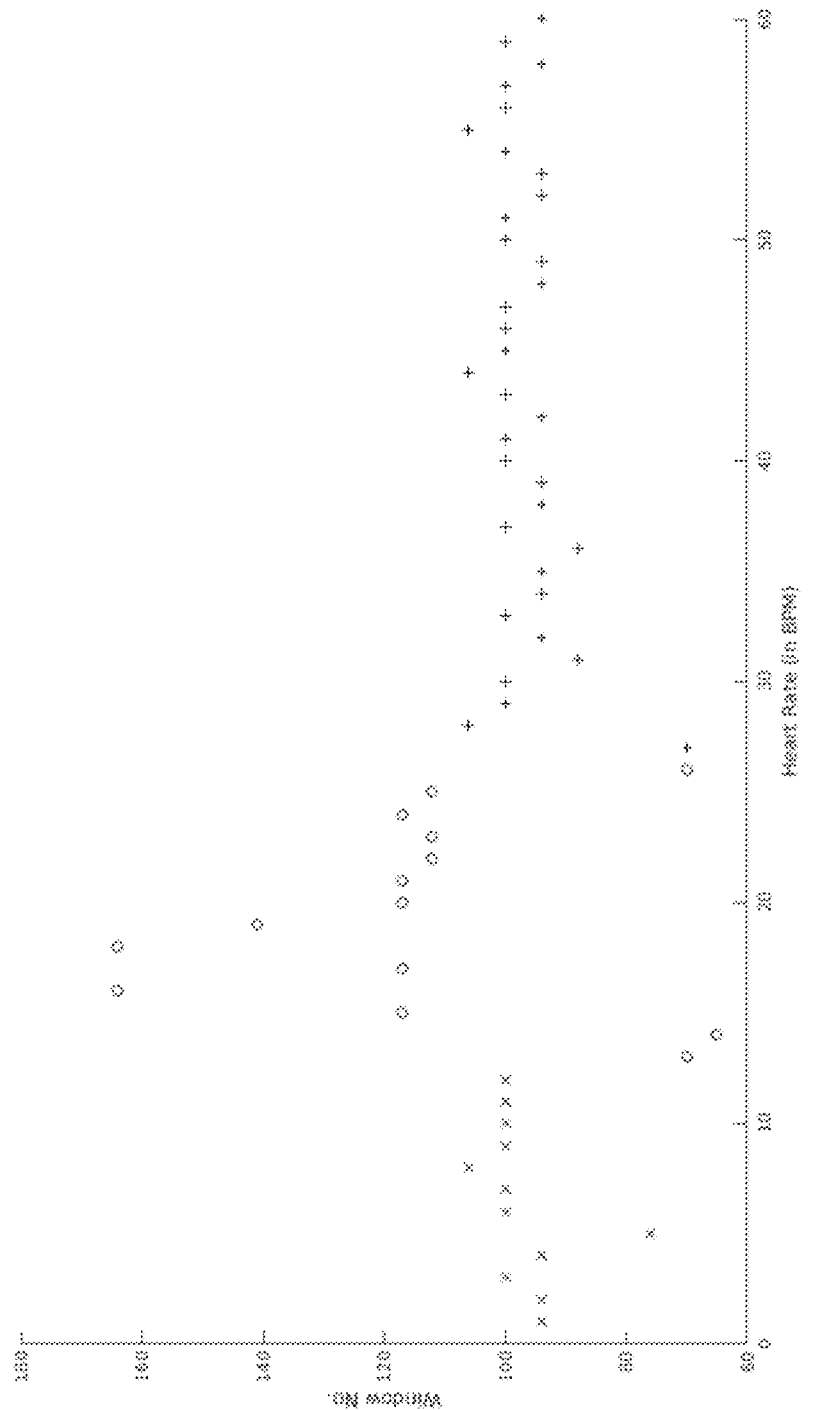
FIG. 6A and FIG. 6B illustrate heart rate values and breathing signal power respectively experienced by an exemplary subject undergoing a treadmill experiment at a speed of 4.2 kmph.
Figure 6B:
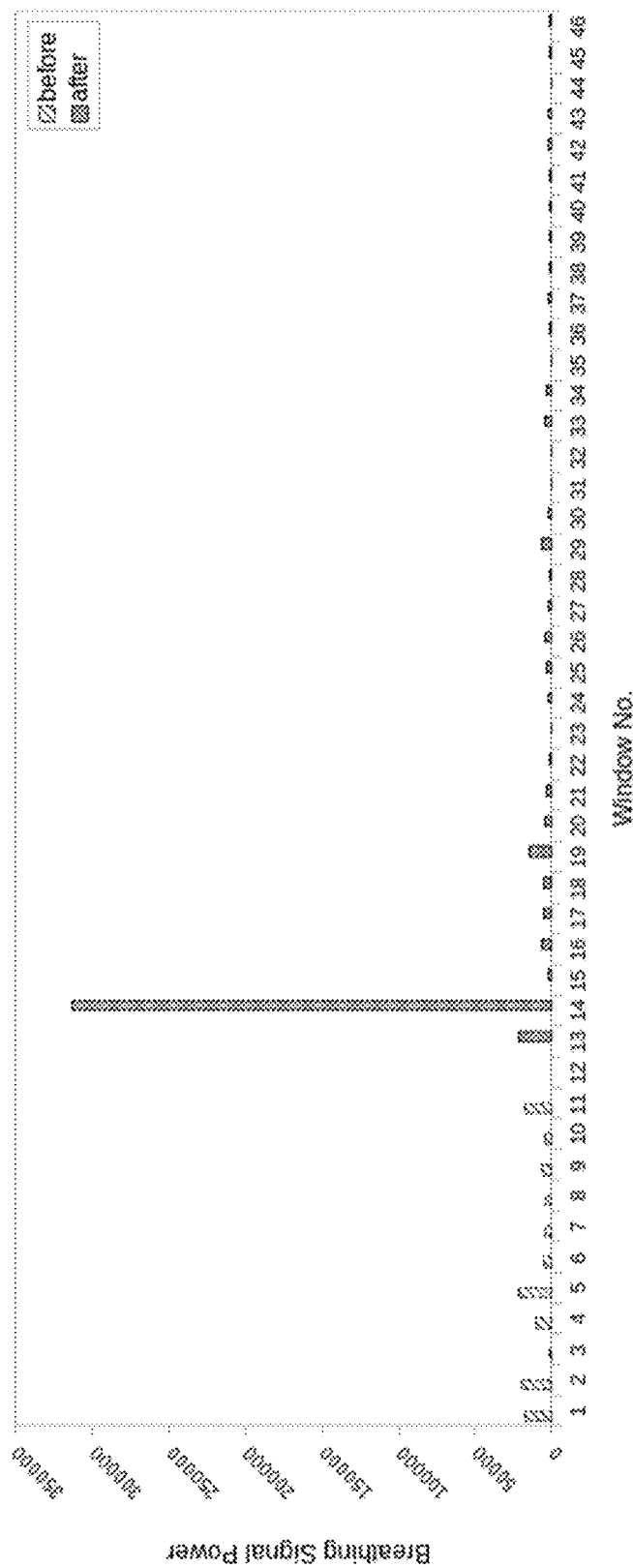
Figure 7A:
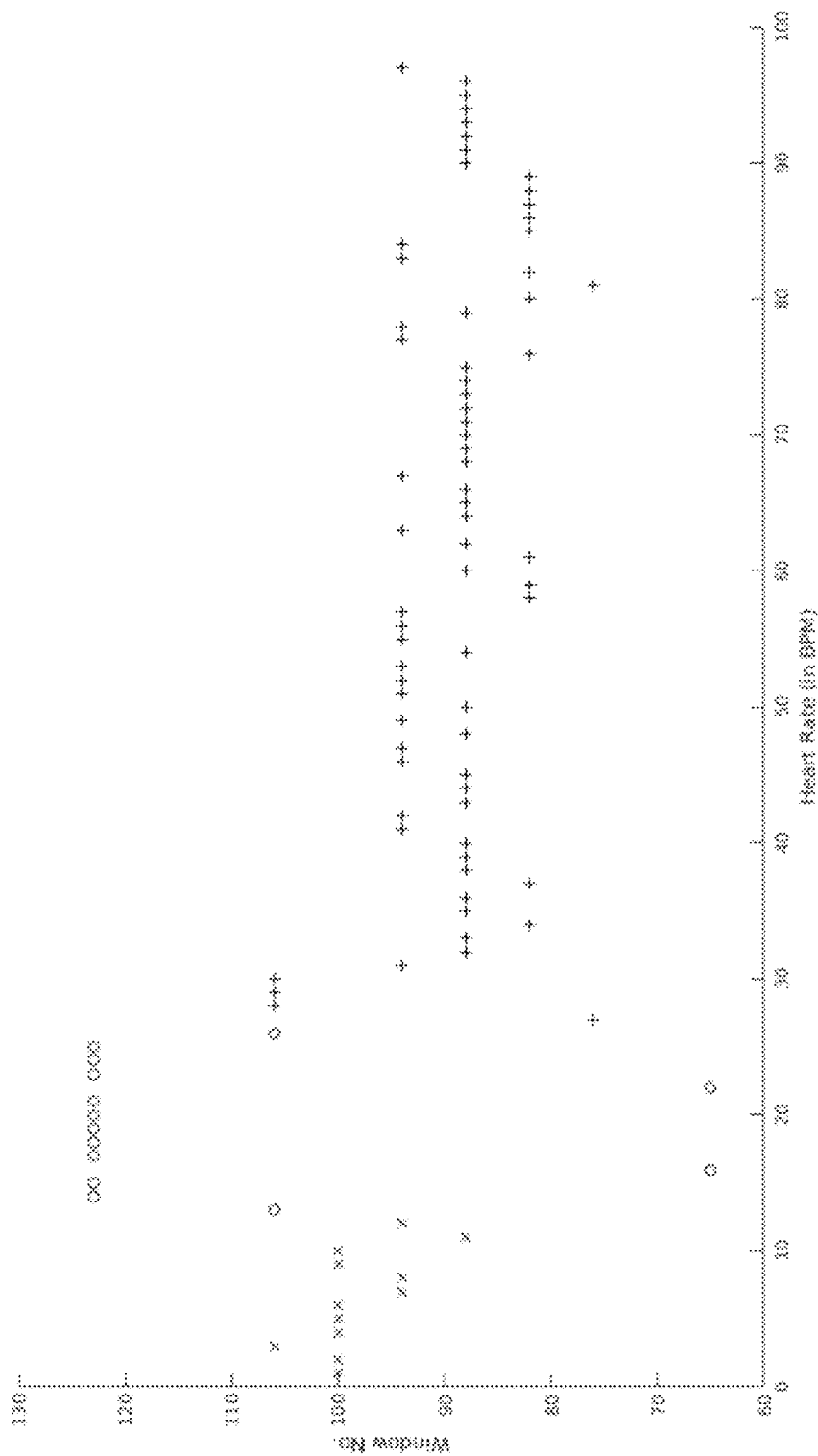
FIG. 7A and FIG. 7B illustrate heart rate values and breathing signal power respectively experienced by the exemplary subject of FIG. 6A and FIG. 6B undergoing a treadmill experiment at a speed of 5.4 kmph.
Figure 7B:
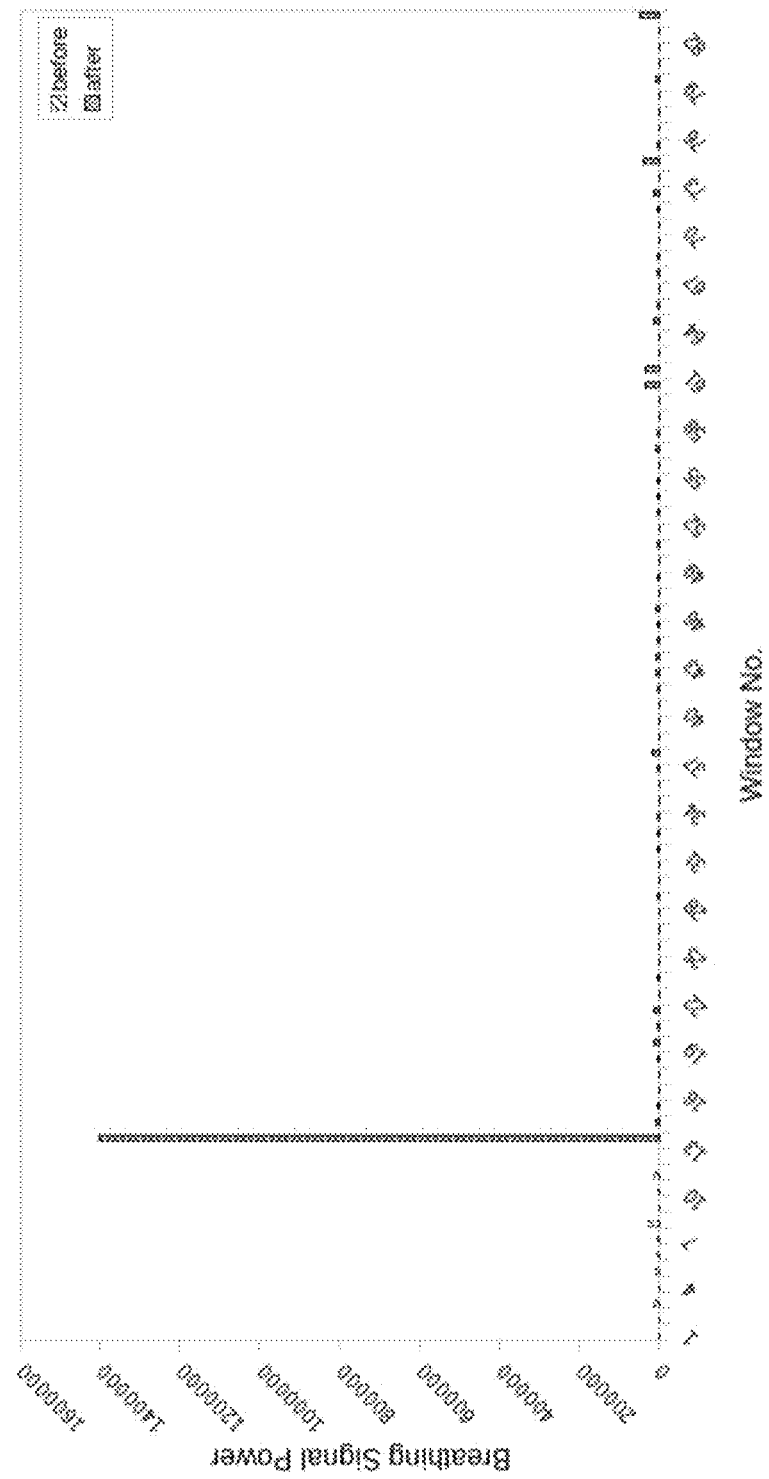

Experimental validation for the method of the present disclosure was performed with high risk subjects walking on a treadmill at different speeds and elevations. Physiological measurements were obtained along with recovery time before and after the walking session. FIG. 6A and FIG. 6B illustrate heart rate values and breathing signal power respectively experienced by an exemplary subject undergoing a treadmill experiment at a speed of 4.2 kmph and FIG. 7A and FIG. 7B illustrate heart rate values and breathing signal power respectively experienced by the exemplary subject of FIG. 6A and FIG. 6B undergoing a treadmill experiment at a speed of 5.4 kmph. It was noted that there was no substantial change in heart rate, no noticeable fatigue was experienced by the high risk subject and breathing power shot up momentarily but settled down very quickly (very less recovery time.

Figure 8A:
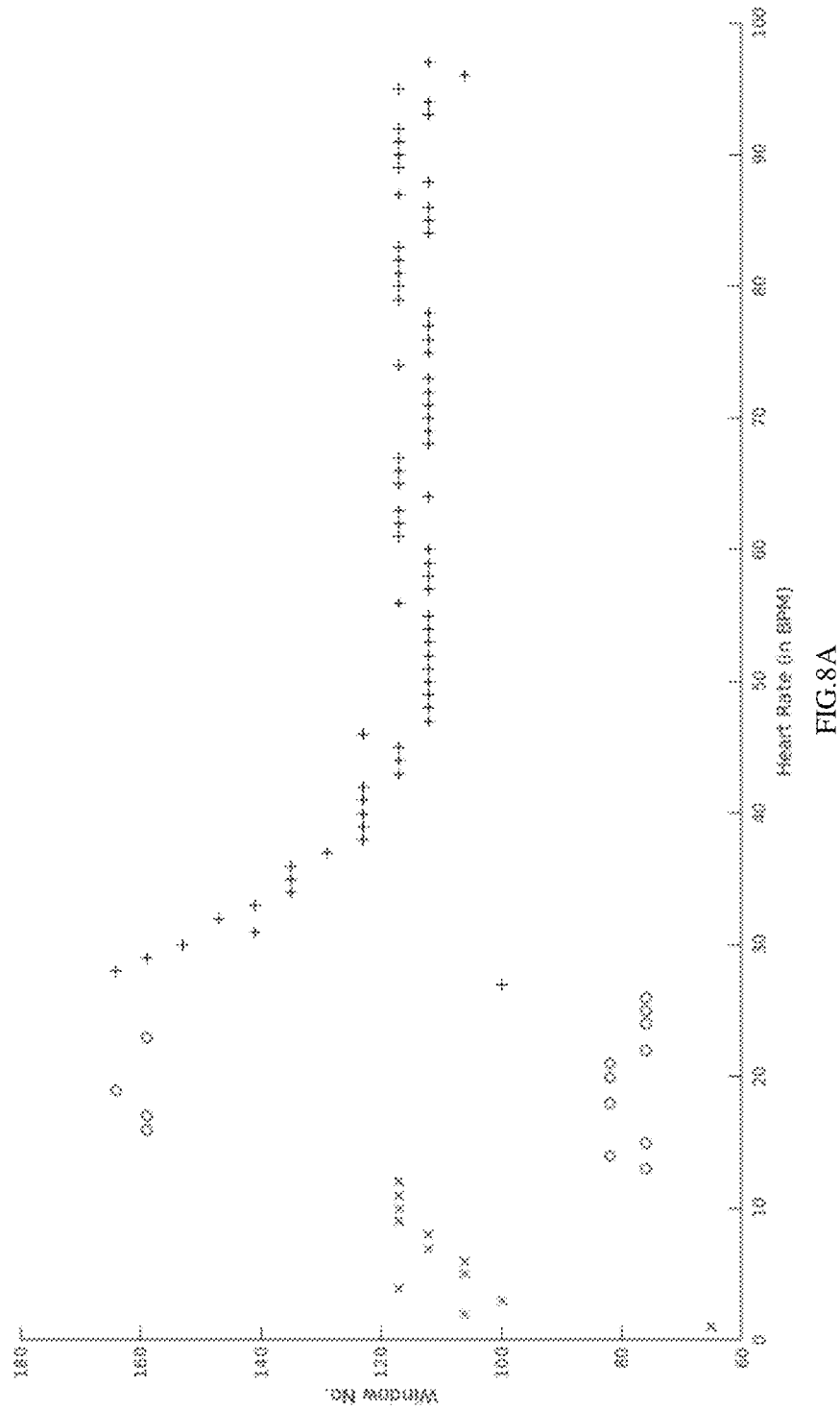
FIG. 8A and FIG. 8B illustrate heart rate values and breathing signal power respectively experienced by the exemplary subject of FIG. 6A and FIG. 6B undergoing a treadmill experiment at a speed of 7.8 kmph.
Figure 8B:
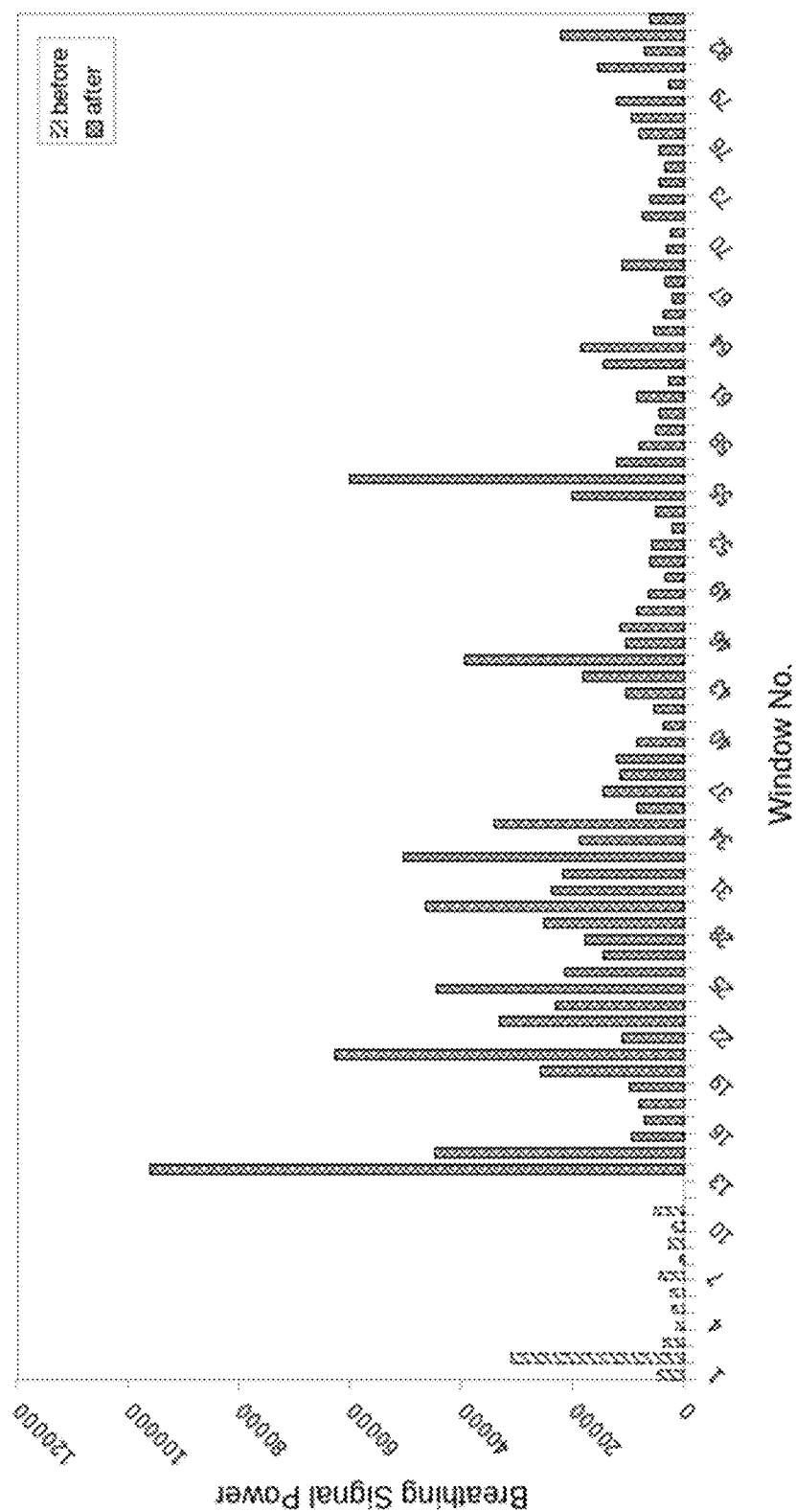
Figure 9A:
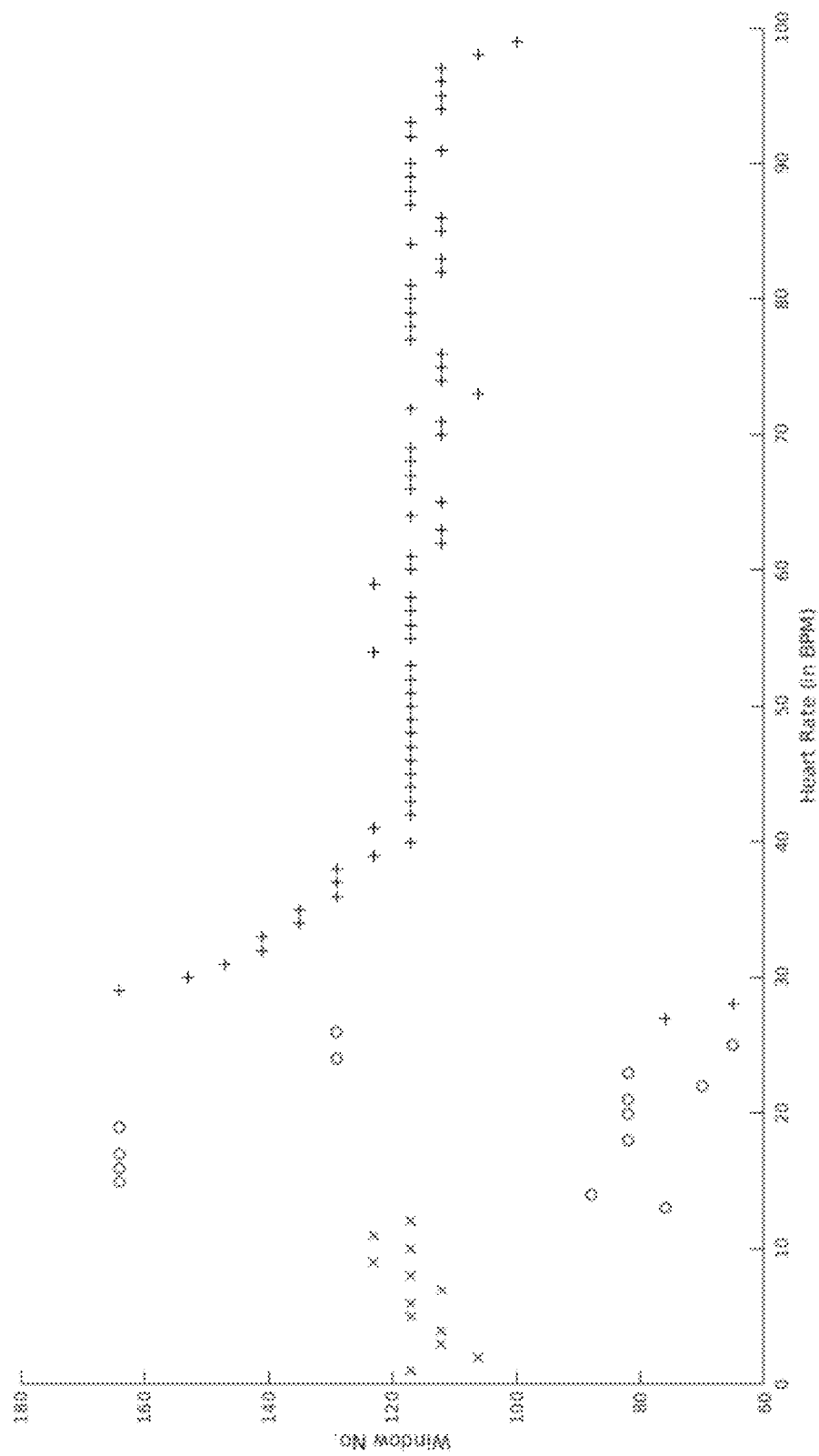
FIG. 9A and FIG. 9B illustrate heart rate values and breathing signal power respectively experienced by the exemplary subject of FIG. 6A and FIG. 6B undergoing a treadmill experiment at a speed of 9.0 kmph.
Figure 9B:
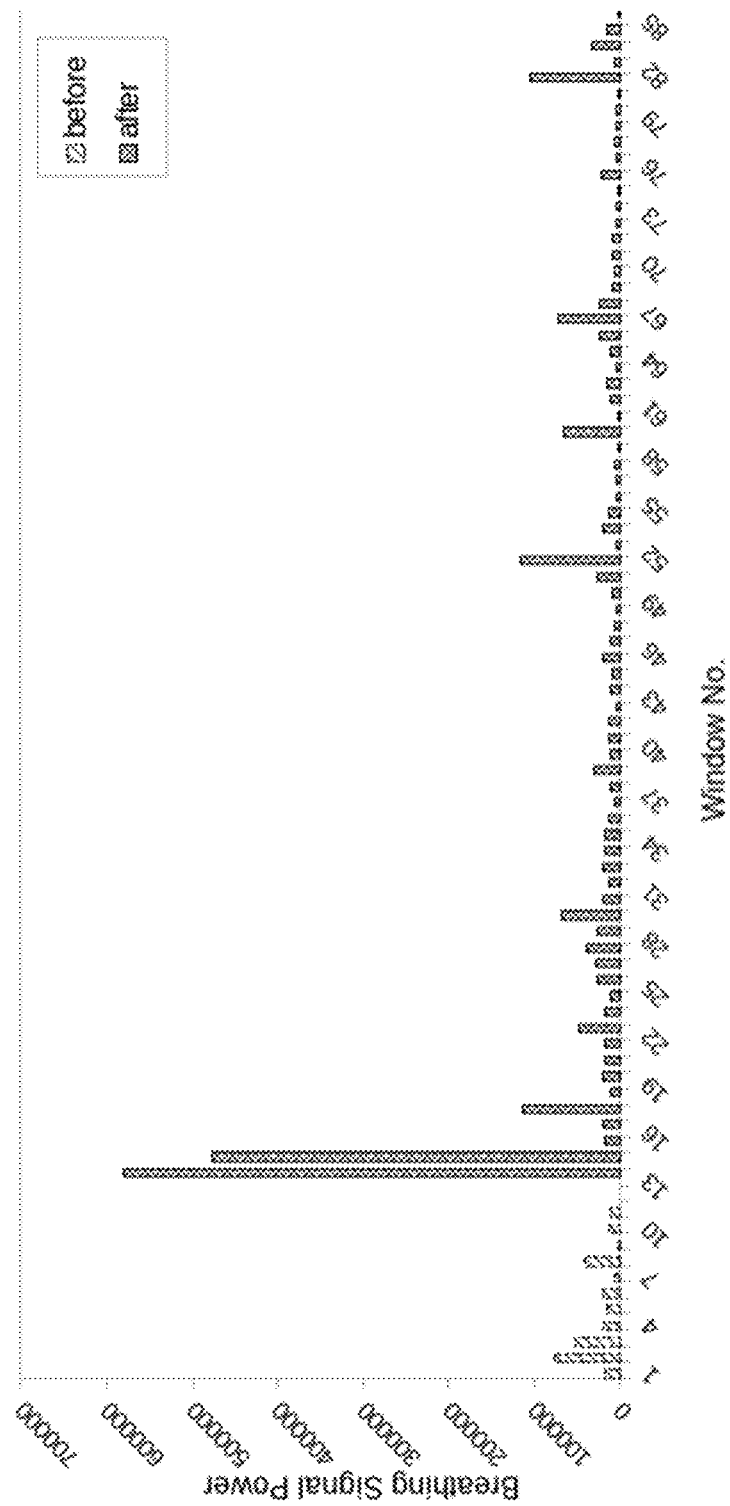

FIG. 8A and FIG. 8B illustrate heart rate values and breathing signal power respectively experienced by the exemplary subject of FIG. 6A and FIG. 6B undergoing a treadmill experiment at a speed of 7.8 kmph and FIG. 9A and FIG. 9B illustrate heart rate values and breathing signal power respectively experienced by the exemplary subject of FIG. 6A and FIG. 6B undergoing a treadmill experiment at a speed of 9.0 kmph. It was noted that there was substantial change in heart rate, shortness of breath and fatigue was reported by the high risk subject under consideration and breathing power increased after the session and settled down gradually reflecting more recovery time. This observation clearly indicates that although the high risk subject under consideration is asymptomatic, further assessment is necessary to diagnose a medical condition, if any, that may need attention.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having,"

"containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
    obtaining a plurality of values associated with a plurality of metadata features associated with a plurality of high risk subjects, wherein
        the plurality of metadata features comprises domain knowledge of the plurality of high risk subjects
        the domain knowledge includes one or more of:
            physical characteristics including height, weight, gender, ethnicity, and age,
            lifestyle habits including smoking, drinking, exercising regularly, and over-eating, and
            prevailing medical conditions,
        the high risk subjects are subjects with predisposing systemic conditions including neuropathy, peripheral arterial disease, diabetes mellitus, proneness to infection, autoimmune disease,
        the plurality of high risk subjects are more likely to get a particular disease than a normal subject,
        a platform integrates the physical characteristics, the lifestyle habits and the prevailing medical conditions including diabetes, hypertension, cardiac illness, anemia, with monitored physical activities and physiological measurements to assess health of the high risk subjects;
    generating groups from the plurality of high risk subjects based on a plurality of combinations of the obtained plurality of metadata features corresponding to one of a combination of the age and the weight associated with the plurality of high risk subjects, the age and the height associated with the plurality of high risk subjects, the age associated with the plurality of high risk subjects, the weight associated with the plurality of high risk subjects and cardiac issues associated with the plurality of high risk subjects; and
    iteratively obtaining a skewed normal distribution of the plurality of high risk subjects;
    automatically generating, based on the obtained skewed normal distribution, a treatment class and a control class for each of the generated groups, obtaining the skewed normal distribution comprising:
    generating a fuzzy membership function using a neural network, wherein the neural network includes a multi-layer perceptron with at least two hidden layers and a fully connected input layer and an output layer; and
    deriving, based on the fuzzy membership function, two feature classes for each of the obtained plurality of metadata features, wherein a feature class of the two feature classes is young or old for the age as a metadata feature of the plurality of metadata features, and the class is tall or short for the height as the metadata feature;
        deriving a plurality of normalized values between 0 and 1 for each of the plurality of high risk subjects in the two derived feature classes, wherein a normalized value of the plurality of normalized values corresponds to the metadata feature;
        obtaining a Manhattan distance between every pair of high risk subjects amongst the plurality of high risk subjects using the plurality of normalized values;
        generating two clusters of the high risk subjects based on the obtained Manhattan distance and using a fuzzy C-means clustering method such that each of the two clusters have equivalent normalized values (206 $d$);
        randomly sampling the two clusters to create the control class and the treatment class such that the control class and the treatment class comprises an equivalent number of the plurality of high risk subjects from each of the two clusters;
        reconstructing the plurality of normalized values associated with each of the plurality of high risk subjects by correlating an identifier of the plurality of high risk subjects with a meta-dictionary to obtain actual values corresponding to the associated metadata features for each of the plurality of high risk subjects in the control class and the treatment class;
    identifying a level of deterioration of health of each of the plurality of high risk subjects in the treatment class by:
        monitoring, via a wearable device and allied mobile or stationary gateways, physical activity levels related to a time spent and a distance achieved while performing walking measured and physiological measurements of the plurality of high risk subjects from the treatment class;
        classifying each of the high risk subjects into one of a plurality of pre-determined classes from I to IV illustrative of health assessment of the high risk subject and depict stages of a heart failure using a computational model and a correlation between the monitored physical activity levels (MET) and the physiological measurements, wherein the computational model is based on New York Heart Association (NYHA) guidelines wherein 4 classes are identified to depict stages of heart failure, wherein Class I is mapped to a condition that ordinary physical activity does not cause undue fatigue, palpitations, dyspnea and/or angina, Class II is mapped to a condition that ordinary physical activity does cause undue fatigue, palpitations, dyspnea and/or angina, Class III is mapped to a condition that less than ordinary physical activity causes undue fatigue, palpitations, dyspnea and/or angina, and Class IV is mapped to a condition that fatigue, palpitations, dyspnea and/or angina occurs at rest, wherein a metadata feature fatigue is modelled in form of I=f (MET, W, T, LPA, G, A, N), where I represents an intensity as a function of intensity associated with the MET, W represents body weight of the high risk subject under consideration, T represents Spell's duration, LPA represents level of physical activity in daily life of the high risk subject under consideration, G represents the gender of the high risk subject under consideration, A represents age spectrum and N represents a normalization constant;

predicting a normalized value for each of the physiological measurements of interest using a Hidden Markov Model (HMM) with stage wise prediction, the physiological parameters being a metabolic equivalents of task (MET), breathing power change, heart rate change, breathing rate change, time taken to return to a Basal heart rate referring to normal heart rate at rest for the high risk subject under consideration and accordingly the Class II is identified if a high risk subject gets tired after predefined minutes of walking;

computing a measure of deviation from the predicted normalized value using an actual normalized value obtained from the monitored physiological measurements to assess deviation from a healthy condition for each of the high risk subjects;

eliminating local outliers in the physiological measurements using a Local Outlier Filter algorithm to obtain filtered physiological measurements (208 e);

performing a trend analyses, of the monitored physical activity levels and the filtered physiological measurements, using AutoRegressive Integrated Moving Average (ARIMA), wherein the ARIMA facilitates in identifying a long term trend when the subject is tired while performing the physical activity; and triggering an alarm when a trend is negative with a slope greater than a pre-defined threshold;

obtaining feedback from the high risk subject pertaining to the monitored physical activity levels and analyzing the feedback to check if the high risk subject feel tired after 2 minutes of walking and the metadata feature associated with tiredness is identified as a bio-marker for further assessment of the high risk subject, wherein physiological parameters monitored before and after the physical activity for a particular metabolic equivalents (MET) are used to assess the levels of cardiopulmonary fatigue in the high risk subject, wherein the fatigue levels of the high risk subject under consideration is normalized considering other high risk subjects in the same group, wherein if a normalized level of the fatigue is higher than a major percentage of population in the group, then the high risk subject is marked for further assessment based on the fatigue level being identified as the bio-marker, wherein the marked high risk subject is monitored longitudinally over time to check if the fatigue levels are trending negatively to trigger a timely alarm, wherein if the fatigue levels are not trending negatively, then pre-op monitoring continues to assess the health of the high risk subject in an unobtrusive manner.

2. The processor implemented method of claim 1, wherein the step of obtaining values associated with a plurality of metadata features comprises (i) directly deriving the values using corresponding measurement devices or (ii) estimating the values based on the domain knowledge of the high risk subjects under consideration.

3. The processor implemented method of claim 1, wherein the random sampling is based on a mean and a standard deviation associated with the obtained skewed normal distribution of the high risk subjects.

4. The processor implemented method of claim 1, further comprising:

accurately monitoring movement patterns of the high risk subject using a motion sensor and checking the physiological measurements including measuring of blood oxygen saturation levels SpO2 using medical devices; and involving a care taker for the high risk subject by a persuasion engine for ensuring post-op care and adhering to requirements of the high risk subject.

5. A system comprising:

one or more data storage devices operatively coupled to one or more hardware processors and configured to store instructions configured for execution by the one or more hardware processors to:

obtain a plurality of values associated with a plurality of metadata features associated with a plurality of high risk subjects, wherein the plurality of metadata features comprises domain knowledge of the plurality of high risk subjects the domain knowledge includes one or more of:
physical characteristics including height, weight, gender, ethnicity, and age,
lifestyle habits including smoking, drinking, exercising regularly, and over-eating, and
prevailing medical conditions, the high risk subjects are subjects with predisposing systemic conditions including neuropathy, peripheral arterial disease, diabetes mellitus, proneness to infection, autoimmune disease, the plurality of high risk subjects are more likely to get a particular disease than a normal subject, a platform integrates the physical characteristics, the lifestyle habits and the prevailing medical conditions including diabetes, hypertension, cardiac illness, anemia, with monitored physical activities and physiological measurements to assess health of the high risk subjects;

generate groups from the plurality of high risk subjects based on a plurality of combinations of the obtained plurality of metadata features corresponding to one of a combination of the age and the weight associated with the plurality of high risk subjects, the age and the height associated with the plurality of high risk subjects, the age associated with the plurality of high risk subjects, the weight and having cardiac issues associated with the plurality of high risk subjects; and iteratively obtain a skewed normal distribution of the plurality of high risk subjects;

automatically generate, based on the obtained skewed normal distribution, a treatment class and a control class for each of the generated groups, wherein the skewed normal distribution is obtained by:

generating a fuzzy membership function using a neural network, wherein the neural network includes a multi-layer perceptron with at least two hidden layers and a fully connected input layer and an output layer; and deriving, based on the fuzzy membership function, two feature classes for each of the obtained plurality of metadata features, wherein a feature class of the two feature classes is young or old for the age as a metadata feature of the plurality of metadata features, and the class is tall or short for the height as the metadata feature;

deriving a plurality of normalized values between 0 and 1 for each of the plurality of high risk subjects in the two derived feature classes, wherein a normalized value of the plurality of normalized values corresponds to a metadata feature;

obtaining a Manhattan distance between every pair of high risk subjects amongst the plurality of high risk subjects using the plurality of normalized values;

generating two clusters of the high risk subjects based on the obtained Manhattan distance and using a fuzzy C-means clustering method such that each of the two clusters have equivalent normalized values;

randomly sampling the two clusters to create the control class and the treatment class such that the control class and the treatment class comprises an equivalent number of plurality of high risk subjects from each of the two clusters;

reconstructing the plurality of normalized values associated with each of the plurality of high risk subjects by correlating an identifier of the plurality of high risk subjects with a meta-dictionary to obtain actual values corresponding to the associated metadata features for each of the plurality of high risk subjects in the control class and the treatment class;

identifying a level of deterioration of health of each of the high risk subjects in the treatment class by:

monitoring, via a wearable device and allied mobile or stationary gateways, physical activity levels related to a time spent and a distance achieved while performing walking measured and physiological measurements of the plurality of high risk subjects from the treatment class;

classifying each of the high risk subjects into one of a plurality of pre-determined classes from I to IV illustrative of health assessment of the high risk subject and depict stages of a heart failure using a computational model and a correlation between the monitored physical activity levels (MET) and the physiological measurements; wherein the computational model is based on New York Heart Association (NYHA) guidelines wherein 4 classes are identified to depict stages of heart failure, wherein Class I is mapped to a condition that ordinary physical activity does not cause undue fatigue, palpitations, dyspnea and/or angina, Class II is mapped to a condition that ordinary physical activity does cause undue fatigue, palpitations, dyspnea and/or angina, Class III is mapped to a condition that less than ordinary physical activity causes undue fatigue, palpitations, dyspnea and/or angina, and Class IV is mapped to a condition that fatigue, palpitations, dyspnea and/or angina occurs at rest, wherein a metadata feature fatigue is modelled in form of $I=f(MET, W, T, LPA, G, A, N)$, where I represents an intensity as a function of intensity associated with the MET, W represents body weight of the high risk subject under consideration, T represents Spell's duration, LPA represents level of physical activity in daily life of the high risk subject under consideration, G represents the gender of the high risk subject under consideration, A represents age spectrum and N represents a normalization constant;

predicting a normalized value for each of the physiological measurements of interest using a Hidden Markov Model (HMM) with stage wise prediction, the physiological parameters being a metabolic equivalents of task (MET), breathing power change, heart rate change, breathing rate change, time taken to return to a Basal heart rate referring to normal heart rate at rest for the high risk subject under consideration and accordingly the Class II is identified if a high risk subject gets tired after predefined minutes of walking;

computing a measure of deviation from the predicted normalized value using an actual normalized value obtained from the monitored physiological measurements to assess deviation from a healthy condition for each of the high risk subjects;

eliminating local outliers in the physiological measurements using a Local Outlier Filter (LOF) algorithm to obtain filtered physiological measurements (208 *e*);

performing a trend analyses, of the monitored physical activity levels and the filtered physiological measurements, using AutoRegressive Integrated Moving Average (ARIMA), wherein the ARIMA facilitates in identifying a long term trend when the subject is tired while performing the physical activity; and triggering an alarm when a trend is negative with a slope greater than a pre-defined threshold;

obtaining feedback from the high risk subject pertaining to the monitored physical activity levels and analyzing the feedback to check if the high risk subject feel tired after 2 minutes of walking and the metadata feature associated with tiredness is identified as a bio-marker for further assessment of the high risk subject, wherein physiological parameters monitored before and after the physical activity for a particular metabolic equivalents (MET) are used to assess the levels of cardiopulmonary fatigue in the high risk subject, wherein the fatigue levels of the high risk subject under consideration is normalized considering other high risk subjects in the same group, wherein if a normalized level of the fatigue is higher than a major percentage of population in the group, then the high risk subject is marked for further assessment based on the fatigue level being identified as the bio-marker, wherein the marked high risk subject is monitored longitudinally over time to check if the fatigue levels are trending negatively to trigger a timely alarm, wherein if the fatigue levels are not trending negatively, then pre-op monitoring continues to assess the health of the high risk subject in an unobtrusive manner.

6. The system of claim 5, wherein the one or more hardware processors are further configured to obtain values associated with a plurality of metadata features by (i) directly deriving the values using corresponding measurement devices or (ii) estimating the values based on the domain knowledge of the high risk subjects under consideration.

7. The system of claim 5, wherein the one or more hardware processors are further configured to randomly sample the two clusters based on a mean and a standard deviation associated with the obtained skewed normal distribution of the high risk subjects.

8. The system of claim 5, wherein the one or more hardware processors are further configured to:
accurately monitor movement patterns of the high risk subject using a motion sensor and checking the physiological measurements including measuring of blood oxygen saturation levels SpO2 using medical devices; and
involve a care taker for the high risk subject by a persuasion engine comprises in the system for ensuring post-op care and adhering to requirements of the high risk subject.

9. A computer program product comprising a non-transitory computer readable medium having a computer readable program embodied therein, wherein the computer readable program, when executed on a computing device, causes the computing device to:
obtain a plurality of values associated with a plurality of metadata features associated with a plurality of high risk subjects, wherein
the plurality of metadata features comprises domain knowledge of the plurality of high risk subjects
the domain knowledge includes one or more of:
physical characteristics including height, weight, gender, ethnicity, and age,
lifestyle habits including smoking, drinking, exercising regularly, and over-eating, and prevailing medical conditions,
the high risk subjects are subjects with predisposing systemic conditions including neuropathy, peripheral arterial disease, diabetes mellitus, proneness to infection, autoimmune disease,
the plurality of high risk subjects are more likely to get a particular disease than a normal subject,
a platform integrates the physical characteristics, the lifestyle habits and the prevailing medical conditions including diabetes, hypertension, cardiac illness, anemia, with monitored physical activities and physiological measurements to assess health of the high risk subjects;
generate groups from of the plurality of high risk subjects based on a plurality of combinations of the obtained plurality of metadata features corresponding to one of a combination of the age and the weight associated with the plurality of high risk subjects, the age and the height associated with the plurality of high risk subjects, the age associated with the plurality of high risk subjects, the weight associated with the plurality of high risk subjects and cardiac issues associated with the plurality of high risk subjects; and
iteratively obtain a skewed normal distribution of the plurality of high risk subjects;
automatically generating, based on the obtained skewed normal distribution, a treatment class and a control class for each of the generated groups, wherein the skewed normal distribution is obtained by:
generating a fuzzy membership function using a neural network, wherein the neural network includes a multi-layer perceptron with at least two hidden layers and a fully connected input layer and an output layer and
deriving, based on the fuzzy membership function, two feature classes for each of the obtained metadata features, wherein feature class is young or old for the age as the metadata feature, and the class is tall or short for the height as the metadata feature, wherein the neural network uses a multi-layer perceptron with at least two hidden layers and a fully connected input layer and output layer;
deriving a plurality of normalized values between 0 and 1 for each of the high risk subjects in the two derived feature classes, wherein a normalized value in the plurality of normalized values corresponds to a metadata feature;
obtaining a Manhattan distance between every pair of subjects amongst the high risk subjects using the plurality of normalized values;
generating two clusters of the high risk subjects based on the obtained Manhattan distance and using a fuzzy C-means clustering method such that each of the two clusters have equivalent normalized values, wherein the fuzzy C-means clustering ensures that an inter-cluster distance is high and an intra-cluster distance is low;
randomly sampling the two clusters to create the control class and the treatment class such that the control class and the treatment class comprises an equivalent number of high risk subjects from each of the two clusters;
reconstructing the plurality of normalized values associated with each of the high risk subjects by correlating an identifier of the high risk subject with a meta-dictionary to obtain actual values corresponding to the associated metadata features for each of the high risk subjects in the control class and the treatment class;
identifying a level of deterioration of health of each of the high risk subjects in the treatment class by:
monitoring, via a wearable device and allied mobile or stationary gateways, physical activity levels related to a time spent and a distance achieved while performing walking measured and physiological measurements of the plurality of high risk high risk subjects from the treatment class;
classifying each of the high risk subjects into one of a plurality of pre-determined classes from I to IV illustrative of health assessment of the high risk subject and depict stages of a heart failure using a computational model and a correlation between the monitored physical activity levels (MET) and the physiological measurements, wherein the computational model is based on New York Heart Association (NYHA) guidelines wherein 4 classes are identified to depict stages of heart failure, wherein Class I is mapped to a condition that ordinary physical activity does not cause undue fatigue, palpitations, dyspnea and/or angina, Class II is mapped to a condition that ordinary physical activity does cause undue fatigue, palpitations, dyspnea and/or angina, Class III is mapped to a condition that less than ordinary physical activity causes undue fatigue, palpitations, dyspnea and/or angina, and Class IV is mapped to a condition that fatigue, palpitations, dyspnea and/or angina occurs at rest,
wherein a metadata feature fatigue is modelled in form of I=f (MET, W, T, LPA, G, A, N), where I represents an intensity as a function of intensity associated with the MET, W represents body weight of the high risk subject under consideration, T represents Spell's duration, LPA represents level of physical activity in daily life of the high risk subject under consideration, G represents the gender of the high risk subject under consideration, A represents age spectrum and N represents a normalization constant;

predicting a normalized value for each of the physiological measurements of interest using a Hidden Markov Model (HMM) with stage wise prediction, the physiological parameters being a metabolic equivalents of task (MET), breathing power change, heart rate change, breathing rate change, time taken to return to a Basal heart rate referring to normal heart rate at rest for the high risk subject under consideration and accordingly the Class II is identified if a high risk subject gets tired after predefined minutes of walking;

computing a measure of deviation from the predicted normalized value using an actual normalized value obtained from the monitored physiological measurements to assess deviation from a healthy condition for each of the high risk subjects;

eliminating local outliers in the physiological measurements using a Local Outlier Filter (LOF) algorithm to obtain filtered physiological measurements (208 e);

performing a trend analyses, of the monitored physical activity levels and the filtered physiological measurements, using AutoRegressive Integrated Moving Average (ARIMA), wherein the ARIMA facilitates in identifying a long term trend when the subject is tired while performing the physical activity; and triggering an alarm when a trend is negative with a slope greater than a pre-defined threshold;

obtaining feedback from the high risk subject pertaining to the monitored physical activity levels and analyzing the feedback to check if the high risk subject feel tired after 2 minutes of walking and the metadata feature associated with tiredness is identified as a bio-marker for further assessment of the high risk subject, wherein physiological parameters monitored before and after the physical activity for a particular metabolic equivalents (MET) are used to assess the levels of cardiopulmonary fatigue in the high risk subject, wherein the fatigue levels of the high risk subject under consideration is normalized considering other high risk subjects in the same group, wherein if a normalized level of the fatigue is higher than a major percentage of population in the group, then the high risk subject is marked for further assessment based on the fatigue level being identified as the bio-marker, wherein the marked high risk subject is monitored longitudinally over time to check if the fatigue levels are trending negatively to trigger a timely alarm, wherein if the fatigue levels are not trending negatively, then pre-op monitoring continues to assess the health of the high risk subject in an unobtrusive manner.

* * * * *